(12) United States Patent
Baek et al.

(10) Patent No.: US 12,097,050 B2
(45) Date of Patent: Sep. 24, 2024

(54) METHODS AND SYSTEMS FOR IMAGE SEGMENTATION AND ANALYSIS

(71) Applicant: UNIVERSITY OF IOWA RESEARCH FOUNDATION, Iowa City, IA (US)

(72) Inventors: Stephen Baek, Coralville, IA (US); Yusen He, Iowa City, IA (US); Xiaodong Wu, Coralville, IA (US); Yusung Kim, Iowa City, IA (US); Bryan G. Allen, Iowa City, IA (US); John Buatti, Iowa City, IA (US); Brian J. Smith, Iowa City, IA (US)

(73) Assignee: UNIVERSITY OF IOWA RESEARCH FOUNDATION, Iowa City, IA (US)

(*) Notice: Subject to any disclaimer, the term of this patent is extended or adjusted under 35 U.S.C. 154(b) by 423 days.

(21) Appl. No.: 17/434,333

(22) PCT Filed: Feb. 27, 2020

(86) PCT No.: PCT/US2020/020158
§ 371 (c)(1),
(2) Date: Aug. 26, 2021

(87) PCT Pub. No.: WO2020/176762
PCT Pub. Date: Sep. 3, 2020

(65) Prior Publication Data
US 2022/0167928 A1    Jun. 2, 2022

Related U.S. Application Data

(60) Provisional application No. 62/811,326, filed on Feb. 27, 2019.

(51) Int. Cl.
*A61B 5/00* (2006.01)
*G06T 7/11* (2017.01)

(52) U.S. Cl.
CPC .......... *A61B 5/7264* (2013.01); *A61B 5/7275* (2013.01); *G06T 7/11* (2017.01);
(Continued)

(58) Field of Classification Search
CPC ....... A61B 5/7264; A61B 5/7275; G06T 7/11; G06T 2200/04; G06T 2207/10081;
(Continued)

(56) References Cited

U.S. PATENT DOCUMENTS 10,950,351 B2 * 3/2021 Madabhushi .......... G16H 50/30
11,023,765 B2 * 6/2021 Lee .......................... A61B 8/06
(Continued)

FOREIGN PATENT DOCUMENTS

| CN | 107644225 A | 1/2018 |
| CN | 109271992 A | 1/2019 |
| WO | WO 2018/222755 A1 | 12/2018 |

OTHER PUBLICATIONS

Written Opinion mailed on May 26, 2018 for PCT/US2020/020158 (9 pages).
(Continued)

*Primary Examiner* — Dhaval V Patel
(74) *Attorney, Agent, or Firm* — Ballard Spahr LLP

(57) ABSTRACT

Methods and systems for image segmentation and analysis are described. A predictive model may be trained to identify and/or extract a rich set of image features with extensive prognostic value. For example, the predictive model may be trained to identify and/or extract features that that may be visualized to identify areas of interest (e.g., high-risk regions, etc.) within or adjacent to an object of interest, such a tumor. The predictive model may be trained to identify and/or extract features that that may predict a health related outcome, such as cancer patient survival/death, and modify therapeutic outcomes, such as diagnosis and treatment.

20 Claims, 9 Drawing Sheets

(52) U.S. Cl.
CPC ............... *G06T 2200/04* (2013.01); *G06T 2207/10081* (2013.01); *G06T 2207/10104* (2013.01); *G06T 2207/20084* (2013.01); *G06T 2207/30096* (2013.01)

(58) Field of Classification Search
CPC . G06T 2207/10104; G06T 2207/20084; G06T 2207/30096; G06T 2207/20081
See application file for complete search history.

(56) References Cited

U.S. PATENT DOCUMENTS

| | | | |
|---|---|---|---|
| 11,049,244 B2* | 6/2021 | Wang | A61B 6/5229 |
| 11,120,312 B2* | 9/2021 | Buckler | G06F 18/29 |
| 2016/0073969 A1 | 3/2016 | Ithapu et al. | |
| 2016/0203599 A1 | 7/2016 | Gillies et al. | |
| 2018/0122082 A1 | 5/2018 | Mukherjee et al. | |
| 2018/0204046 A1 | 7/2018 | Bhattacharya et al. | |
| 2020/0134363 A1* | 4/2020 | Hubenig | G06N 20/00 |
| 2020/0226748 A1* | 7/2020 | Kaufman | G06F 18/254 |

OTHER PUBLICATIONS

Satoh, Y. et al. Volume-based parameters measured by using FDG PET/CT in patients with stage I NSCLC treated with stereotactic body radiation therapy: prognostic value. Radiology 270, 275-281 (2014).
Fischer, B. et al. Preoperative staging of lung cancer with combined pet-ct. New Engl. J. Medicine 361, 32-39 (2009).
Oikonomou, A. et al. Radiomics analysis at pet/ct contributes to prognosis of recurrence and survival in lung cancer treated with stereotactic body radiotherapy. Scientific Reports 8(1), 4003, (2018).
De Jong, E. E. et al. Applicability of a prognostic ct-based radiomic signature model trained on stage i-iii non-small cell lung cancer in stage iv non-small cell lung cancer. Lung Cancer 124, 6-11 (2018).
Berghmans, T. et al. Primary tumor standardized uptake value (suvmax) measured on fluorodeoxyglucose positron emission tomography (fdg-pet) is of prognostic value for survival in non-small cell lung cancer (nsclc): A systematic review and meta-analysis (ma) by the european lung cancer working party for the iaslc lung cancer staging project. J. Thorac. Oncol. 3, 6-12, DOI: https://doi.org/10.1097/JTO.0b013e31815e6d6b (2008).
Paesmans, M. et al. Primary tumor standardized uptake value measured on fluorodeoxyglucose positron emission tomography is of prognostic value for survival in non-small cell lung cancer: Update of a systematic review and meta-analysis by the European lung cancer working party for the international association for the study of lung cancer staging project. J. Thorac. Oncol. 5, 612-619, DOI: https://doi.org/10.1097/JTO.0b013e3181d0a4f5 (2010).
Bollineni, V. R., Widder, J., Pruim, J., Langendijk, J. A. & Wiegman, E. M. Residual 18f-fdg-pet uptake 12 weeks after stereotactic ablative radiotherapy for stage i non-small-cell lung cancer predicts local control. Int. J. Radiat. Oncol. 83, e551-e555, DOI: https://doi.org/10.1016/j.ijrobp.2012.01.012 (2012).
Larson, S. M. et al. Tumor treatment response based on visual and quantitative changes in global tumor glycolysis using pet-fdg imaging: The visual response score and the change in total lesion glycolysis. Clin. Positron Imaging 2, 159-171, DOI: https://doi.org/10.1016/S1095-0397(99)00016-3 (1999).
Liao, S. et al. Prognostic value of metabolic tumor burden on 18f-fdg pet in nonsurgical patients with non-small cell lung cancer. Eur. J. Nucl. Medicine Mol. Imaging 39, 27-38, DOI: 10.1007/s00259-011-1934-6 (2012).
Chen, H. H., Chiu, N.-T., Su, W.-C., Guo, H.-R. & Lee, B.-F. Prognostic value of whole-body total lesion glycolysis at pretreatment fdg pet/ct in non-small cell lung cancer. Radiology 264, 559-566 (2012).
Zaizen, Y. et al. Prognostic significance of total lesion glycolysis in patients with advanced non-small cell lung cancer receiving chemotherapy. Eur. J. Radiol. 81, 4179-4184, DOI: https://doi.org/10.1016/j.ejrad.2012.07.009 (2012). Imaging in Acute Chest Pain.
Mehta, G., Chander, A., Huang, C., Kelly, M. & Fielding, P. Feasibility study of fdg pet/ct-derived primary tumour glycolysis as a prognostic indicator of survival in patients with non-small-cell lung cancer. Clin. Radiol. 69, 268-274, DOI: https://doi.org/10.1016/j.crad.2013.10.010 (2014).
Burdick, M. J. et al. Maximum standardized uptake value from staging fdg-pet/ct does not predict treatment outcome for early-stage non-small-cell lung cancer treated with stereotactic body radiotherapy. Int. J. Radiat. Oncol. 78, 1033-1039, DOI: https://doi.org/10.1016/j.ijrobp.2009.09.081 (2010).
Agarwal, M., Brahmanday, G., Bajaj, S. K., Ravikrishnan, K. P. & Wong, C.-Y. O. Revisiting the prognostic value of preoperative 18f-fluoro-2-deoxyglucose (18f-fdg) positron emission tomography (pet) in early-stage (i & ii) non-small cell lung cancers (nsclc). Eur. J. Nucl. Medicine Mol. Imaging 37, 691-698, DOI: 10.1007/s00259-009-1291-x (2010).
Havaei, M. et al. Brain tumor segmentation with deep neural networks. Med. image analysis 35, 18-31 (2017).
Yasaka, Koichiro et al. Deep-learning with convolutional network for differentiation of liver masses at dynamic contrast-enhanced CT: a preliminary study. *Radiology* 286, No. 3, 887-896, DOI: 10.1148/radiol.2017170706 (2017).
Ronneberger, O. et al. U-net: Convolutional networks for biomedical image segmentation. In *International Conference on Medical image computing and computer-assisted intervention*, 234-241 (Springer 2015).
American Lung Association. (Dec. 14, 2018). Lung Cancer Fact Sheet. https://www.lung.org/lung-health-and-diseases/lung-disease-lookup/lung-cancer/resource-library/lung-cancer-fact-sheet.html. (7 pages).
American Cancer Society. (Feb. 4, 2019). Non-Small Cell Lung Cancer Survival Rates. https://www.cancer.org/cancer/non-small-cell-lung-cancer/detection-diagnosis-staging/survival-rates.html (3 pages).
A. Marusyk, V. Almendro, K. Polyak, "Intra-tumour heterogeneity: a looking glass for cancer?," Nat Rev Cancer 12, 323-334 (2012).
G. Lee, H.Y. Lee, H. Park, M.L. Schiebler, E.J.R. van Beek, Y. Ohno, J.B. Seo, A. Leung. Radiomics and its emerging role in lung cancer research, imaging biomarkers and clinical management: State of the art. *Eur J Radiol* 86, 297-307 (2017).
F. Yang, M.A. Thomas, F. Dehdashti, P.W. Grigsby. Temporal analysis of intratumoral metabolic heterogeneity characterized by textural features in cervical cancer. *Eur J Nucl Med Mol Imaging* 40, 716-727 (2013).
Zhao, X. et al. A deep learning model integrating FCNNs and CRFs for brain tumor segmentation. *Medical Image Analysis* 43, 98-111 (2018).
Boneau, C. A. The effects of violations of assumptions underlying the t-test. *Psychological bulletin*, 57, No. 1, 49-64 (1960).
Tibshirani, Robert. Regression Shrinkage and Selection via the lasso. *Journal of the Rotal Statistical Society. Series B (methodological)* 58, No. 1, 267-288 (1996).
Efron, B., Tibshirani, R. *An Introduction to the Bootstrap*. Boca Raton, FL: Chapman & Hall/CRC, (1993). (11 pages).
Yosinski, Jason., et al. Understanding neural networks through deep visualization. *arXiv preprint* arXiv:1506.06579. (12 pages).
Selvaraju, R.R., Cogswell, M., Das, A., Vedantam, R., Parikh, D. and Batra, D. Grad-cam: Visual explanations from deep networks via gradient-based localization. In *Proceedings of the IEEE International Conference on Computer Vision*, 618-626 (2017).
Zhong, Z., et al. 3D fully convolutional networks for co-segmentation of tumors on PET-CT images. In 2018 IEEE 15th International Symposium on Biomedical Imaging (ISBI 2018), 228-231 (2018).
Zhong, Z., Kim, Y., Plichta, K., Allen, B. G., Zhou, L., Buatti, J., & Wu, X. Simultaneous cosegmentation of tumors in PET-CT images using deep fully convolutional networks. Medical physics, (2018).
Aerts et al. (2014). Decoding tumor phenotype by noninvasive imaging using a quantitative radiomics approach. Nature Communications. doi:10.1038/ncomms5006 (8 pages).

(56) References Cited

OTHER PUBLICATIONS

Yamamoto, T. et al. Formula corrected maximal standardized uptake value in fdg-pet for partial volume effect and motion artifact is not a prognostic factor in stage i non-small cell lung cancer treated with stereotactic body radiotherapy. Annals nuclear medicine 29, 666-673 (2015).
Parekh, V. S. et al. Multiparametric deep learning tissue signatures for a radiological biomarker of breast cancer: Preliminary results. arXiv preprint arXiv:1802.08200 (2018).(14 pages).
Wu, X., Zhong, Z., Buatti, J. & Bai, J. Multi-scale segmentation using deep graph cuts: Robust lung tumor delineation in mvcbct. In Biomedical Imaging (ISBI 2018), 2018 IEEE 15th International Symposium on, 514-518 (IEEE, 2018). (11 pages).
Johnson, J., Alahi, A., & Fei-Fei, L . . . Perceptual losses for real-time style transfer and super-resolution. In European Conference on Computer Vision, pp. 694-711. Springer, Cham. (2016).
Chen et al. "Deep Feature Learning for Medical Image Analysis with Convolutional Autoencoder Neural Network." In: IEEE Transactions on Big Data, Jun. 20, 2017 (10 pages).
Wang et al. "Unsupervised Deep Learning Features for Lung Cancer Overall Survival Analysis." In: 40th Annual International Conference of the IEEE Engineering in Medicine and Biology Society (EMBC), Jul. 18-21, 2018 (4 pages).
Beichel, Reinhard R., Brian J. Smith, Christian Bauer, Ethan J. Ulrich, Payam Ahmadvand, Mikalai M. Budzevich, Robert J. Gillies, et al. "Multi-Site Quality and Variability Analysis of 3D FDG PET Segmentations Based on Phantom and Clinical Image Data." Medical Physics 44, No. 2 (Feb. 2017): 479-96.
Byrd, Darrin, Rebecca Christopfel, John Buatti, Eduardo Moros, Sadek Nehmeh, Adam Opanowski, and Paul Kinahan. "Multicenter Survey of PET/CT Protocol Parameters That Affect Standardized Uptake Values." Journal of Medical Imaging (Bellingham, Wash.) 5, No. 1 (Jan. 2018): 011012. (10 pages).
Fedorov, Andriy, David Clunie, Ethan Ulrich, Christian Bauer, Andreas Wahle, Bartley Brown, Michael Onken, et al. "DICOM for Quantitative Imaging Biomarker Development: A Standards Based Approach to Sharing Clinical Data and Structured PET/CT Analysis Results in Head and Neck Cancer Research." PeerJ 4 (2016): e2057. (35 pages).
Ma, Zongqing, Shuang Zhou, Xi Wu, Heye Zhang, Weijie Yan, Shanhui Sun, and Jiliu Zhou. "Nasopharyngeal Carcinoma Segmentation Based on Enhanced Convolutional Neural Networks Using Multi-Modal Metric Learning." Physics in Medicine and Biology 64, No. 2 (Jan. 8, 2019): 025005. (14 pages).
Song, Qi, Junjie Bai, Dongfeng Han, Sudershan Bhatia, Wenqing Sun, William Rockey, John E. Bayouth, John M. Buatti, and Xiaodong Wu. "Optimal Co-Segmentation of Tumor in PET-CT Images with Context Information." IEEE Transactions on Medical Imaging 32, No. 9 (Sep. 2013): 1685-97.

\* cited by examiner

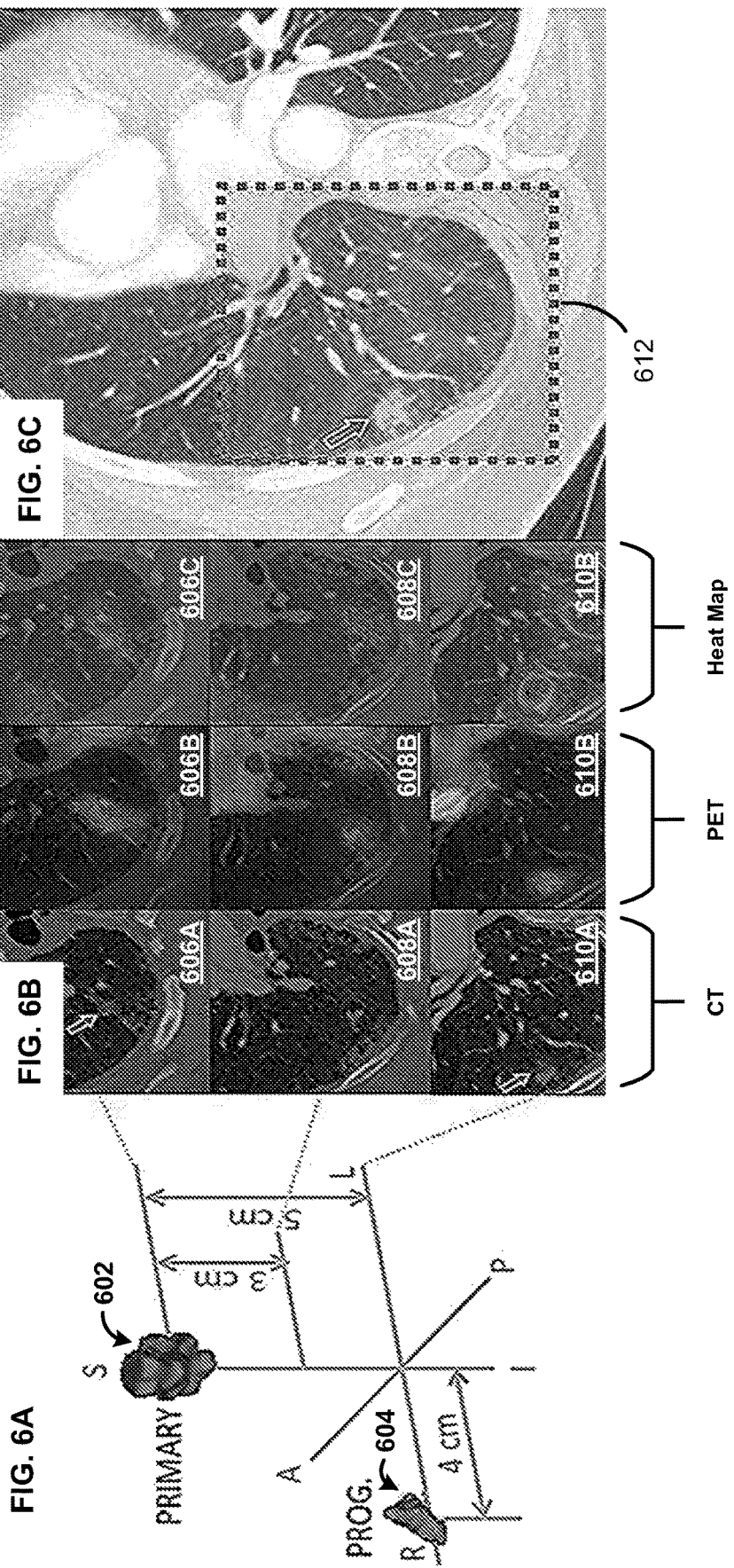

- 710: RECEIVE A PLURALITY OF MEDICAL IMAGES
- 720: GENERATE, FOR EACH OF THE PLURALITY OF MEDICAL IMAGES, A BINARY MASK ASSOCIATED WITH AN OBJECT OF INTEREST IN EACH MEDICAL IMAGE
- 730: PROVIDE THE PLURALITY OF VOLUMETRIC IMAGES AND THE GENERATED BINARY MASK FOR EACH MEDICAL IMAGE TO A UNTRAINED PREDICTIVE MODEL
- 740: DETERMINE ONE OR MORE LATENT PARAMETERS ASSOCIATED WITH THE OBJECT OF INTEREST IN EACH MEDICAL IMAGE
- 750: GENERATE A TRAINED PREDICTIVE MODEL
- 760: GENERATE ONE OR MORE IMAGES INDICATIVE OF A PROGNOSIS

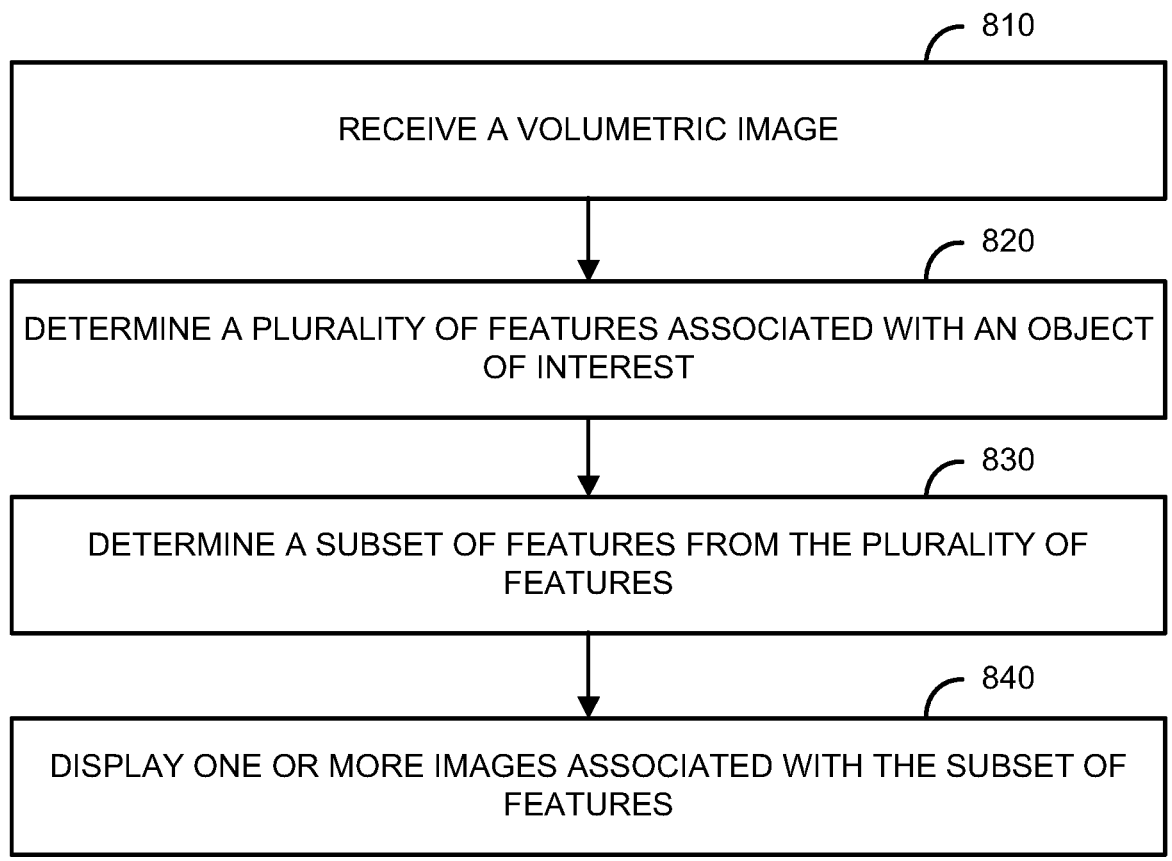

METHODS AND SYSTEMS FOR IMAGE SEGMENTATION AND ANALYSIS

CROSS REFERENCE TO RELATED PATENT APPLICATIONS AND GOVERNMENT SUPPORT CLAUSE

This is a U.S. National Phase Application of International Application No. PCT/US2020/020158, filed on Feb. 27, 2020, which claims priority to U.S. Provisional Application No. 62/811,326, filed on Feb. 27, 2019, each of which are incorporated by reference in their entireties herein. This invention was made with Government support under R21 CA209874 awarded by the National Institutes of Health. The Government has certain rights in the invention.

BACKGROUND

Rapid and robust prognostication of therapeutic outcome is of utmost importance, particularly in relation to cancer treatment. Existing image analysis methods are unable to produce features from medical images with sufficient prognostic value. For example, methods, such as the maximum and the mean of standard uptake value (SUV) and total lesion glycolysis (TLG), determining functional features for non-small-cell lung cancer (NSCLC) prognostication produce unintelligible/uninterpretable features with little to no prognostic value. Machine learning and deep artificial neural networks performing image segmentation and analysis may perform benign and/or malignant tissue classification and tumor segmentation, but are unable to identify instances of metastasis and recurrence that may be prognostic patient survival and/or death.

SUMMARY

Described are methods comprising receiving, from a database, a plurality of medical images, generating, for each of the plurality of medical images, a binary mask associated with an object of interest in each medical image, providing the plurality of medical images and the generated binary mask for each medical image to an untrained predictive model, determining, by the untrained predictive model, for each of the plurality of medical images, one or more latent parameters associated with the object of interest in each medical image, generating, based on the one or more latent parameters associated with the object of interest in each of the plurality of medical images, a trained prediction model, and generating, by the trained predictive model, one or more images indicative of a prognosis.

Also described are methods comprising receiving, by a predictive model comprising a plurality of layers, a medical image, determining, at each of one or more layers of the plurality of layers, a plurality of features associated with an object of interest in the medical image, determining a subset of features of the plurality of features determined for a layer of the one or more layers, wherein the layer comprises a plurality of neurons, and causing, based on one or more neurons of the plurality of neurons, display of one or more images associated with the subset of features, wherein each image of the one or more images is associated with a neuron of the one or more neurons.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate embodiments and together with the description, serve to explain the principles of the methods and systems:

FIGS. 6A-6C show correlations between images generated by an example system for image segmentation and analysis;

FIG. 7 shows a flowchart of an example method for image segmentation and analysis;

FIG. 8 shows a flowchart of an example method for image segmentation and analysis.

DETAILED DESCRIPTION

Figure 1:
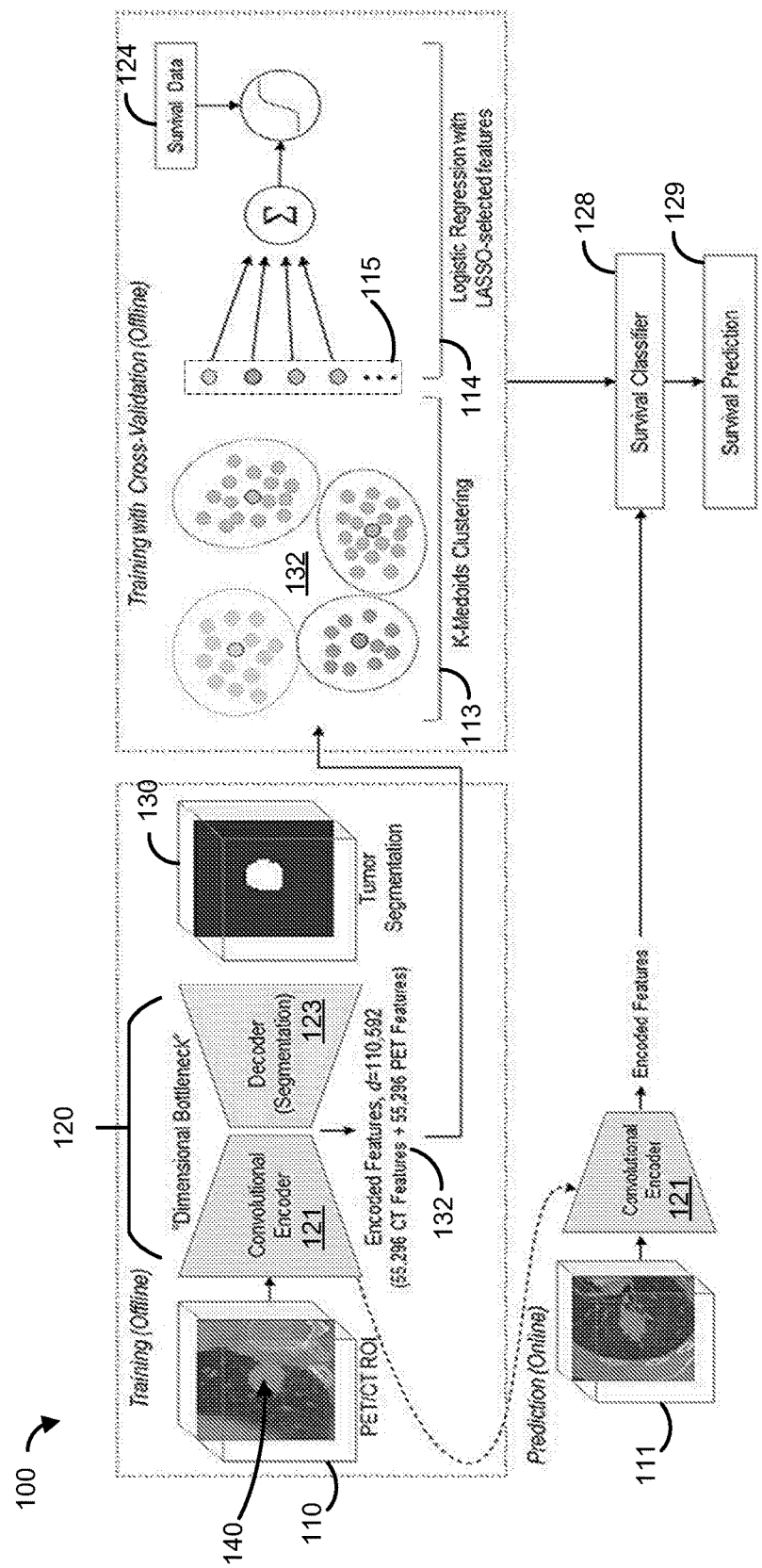
FIG. 1 shows an example system for image segmentation and analysis.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Method and systems described for image segmentation and analysis. Medical imaging and neural networks used in medical analysis is described in Publication "Deep segmentation networks predict survival of non-small cell lung cancer" by Baek, et al. (2019) which is incorporated herein by reference in its entirety. A trained predictive system (e.g., a machine learning model, etc.) may perform image segmentation and analysis. An image, such as a two-dimensional (2D) medical image or a three-dimensional (3D) medical image may be input to the predictive system and processed by a "bottleneck layer" where image features are compressed and reconstructed into a binary segmentation map that indicates a pixel-wise tumor classification result. For example, one or more images that include regions-of-interest (ROIs), such as of tumor tissue sites and/or the like, may be segmented and analyzed to determine a rich set of image-based features with significant prognostic value. Determined features may be visualized to provide detailed prognostic data/information, such as data/information that may be used to pinpoint high-risk regions of metastasis and cancer recurrence, visualize high-risk regions within and/or adjacent to a primary tumor in relation to one or more therapeutic outcomes, and optimize therapeutic strategies.

FIG. 1 shows a schematic diagram of a system 100 for image segmentation and analysis. The system 100 may include analytical model 120. The analytical model 120 that may be trained to generate/determine and output data/information (e.g., a predictive output, etc.), such as a prediction of cancer survival (e.g., survival of non-small cell lung cancer, etc.) and/or the like.

The analytical model 120 may include a multilayer convolutional encoder-decoder neural network and/or any other machine learning model configured for image segmentation and analysis. For example, analytical model 120 may include a convolutional encoder 121 and a decoder 123 that form a "dimensional bottleneck" within the analytical model 120. The dimensional bottleneck 121,123 may be used to obtain a representation of an input with reduced dimensionality. For example, the dimensional bottleneck 121,123 may be used to extract and analyze (visualize) features from images of various modalities (e.g., positron emission tomography (PET) images, computed tomography (CT) images, medical resonance imaging (MRI) images, elastography images, ultrasound images, etc.). The convolutional encoder 121 may include a plurality of neural network layers that each execute a feature extraction process based on an input image and/or imaging data/information.

Images and/or image data from various modalities may be used to train the analytical model 120 to provide a predictive output. A plurality of images, such as co-registered PET-CT images from a plurality of patients/subjects, may be used to form one or more datasets that are used to train the analytical model 120 to provide a predictive output, such as a cancer patient survival/death and/or tumor tissue developmental prediction/analysis. The convolutional encoder 121 may receive a plurality of images, such as an image 110, as input. The image 110 may be a three-dimensional volumetric image that depicts a subject and/or a portion of a subject (e.g., a tumor and surrounding tissue, etc.), such as a PET/CT image and/or any type of imaging data/information. For example, the image 110 may be an image of a tumor tissue (e.g., one or more tumors, etc.) within a subject. The image 110 may include a region of interest (ROI) with a dimension of 96 mm×96 mm×48 mm set around the location (proximity) of an object of interest, such as a tumor 140. In some instances, the image 110 may be cropped to the ROI volume (e.g., a 96×96×48 volume image, etc.). In some instances, the convolutional encoder 121 may receive an image associated with any imaging modality and of any volumetric/3D dimensions. In some instances, the convolutional encoder 121 may receive an image associated with any imaging modality and of any dimensions, such as a two-dimensional (2D) medical image and/or the like.

When training the analytical model 120 data/information associated with each image of the plurality of images may be used to form one or more datasets. For example, a plurality of images depicting tumor tissue at various stages may be used when training the analytical model 120 to predict cancer patient survival/death. In some instances, tumor contour (data/information) associated with each of a plurality of images with a slice image size of 512×512 (and the number of slices may vary from 112 to 293) may be used to form one or more datasets. In some instances, data/information associated with any object of interest (e.g., a tumor, etc.) within each of a plurality of images with any slice image size and any number of slices may be used to form one or more datasets The datasets may be unlabeled datasets, such as datasets that exclude any data/information (e.g., survival data 124, demographic data, behavioral data, etc.) regarding patients associated with the plurality of images, any/or any labeling of objects (e.g., tissue types, plasma/fluids, etc.) depicted within the plurality of images. The datasets may be unlabeled datasets to enable the analytical model 120 to determine/learn features associated with each of the plurality of images. When forming the datasets, the plurality of images may be resampled with an isotropic spacing of 1×1×1 in voxels and then cropped at a fixed size of 3D volumes (96×96×48) centered on the mass gravity of each tumor. Data augmentation may be performed using simple translation (e.g., rotation and flip, etc.). The plurality of images and the datasets may be input/provided to the analytical model 120. The analytical model 120 may be trained and/or may learn to produce a plurality of features for each image (and/or imaging modality) of the plurality of images input to the analytical model 120.

The convolutional encoder 121 may include a plurality of neural network layers that each execute a feature extraction process based on the image 110. Convolutional kernels of the convolutional encoder 121 may be of any size/dimension throughout the network layers. In some instances, convolutional kernels of the convolutional encoder 121 may be of a size 3×3×3 voxels across all layers, and max-pooling layers of a 2×2×2 voxel window size with a stride of 2 may be used for down-sampling. For example, the convolutional encoder 121 may include a first convolution layer that produces 32 feature attributes attached to each voxel of the volume image. The 32 feature attributes may represent low-level visual cues such as lines, edges, and blobs. The features may be down-sampled, for example, by half in all three dimensions. The down-sampled volume may be input to a second convolution layer of the convolutional encoder 121 that produces 64 features per voxel. The process may be repeated for three more times through which the number of features may be increased to 128, 256, and 512, respectively. The volume size may be reduced by half in all three dimensions each time. In some instances the convolutional encoder 121 may process features through any number of layers. The convolutional encoder 121 may produce an output total of features, such as a final 6×6×3×512 (=55,296), that represents an abstract, high-level summary of the input image (e.g., the image 110, etc.). As such, the analytical model 120 (the convolutional encoder 121) may learn to encode at least 55,296 features for each image input to the analytical model 120. For example, the analytical model 120 (the convolutional encoder 121) may learn to encode the features 132. The encoded features 132 may include 110,592 features (55,296 CT features and 55,296 PT features). In some instances, the analytical model 120 (the convolutional encoder 121) may learn to encode any number of features based on any imaging modality. Features may be learned independent without any labeled data, such as survival data 124. In some instances, learned features may be validated based on labeled data, such as the survival data 124.

Cluster analysis may be performed on features encoded from images (e.g., the features 132, etc.) to determine/select representative features from a large pool of inter-correlated features. Any clustering algorithm may be applied to extracted (learned) features. For example, cluster analysis may be used to reduce incidents of statistical overfitting and to differentiate between different types of tissue in an image, such as the image 110. In some instances, k-medoids clustering 113 may be applied to the encoded (and/or extracted) features (e.g., the features 132, etc.) in an unsupervised manner. In some instances, Pearson's correlation distance may be employed as a distance metric for clustering the features as expressed in:

$$\mathcal{D}(X, Y) = 1 - \frac{\text{Cov}(X, Y)}{\sqrt{\text{Var}(X, Y)\text{Var}(X, Y)}}$$

where X and Y denote the two distinct features; Cov( ) denotes the covariance of the two features and Var( ) is the variance of the underlying feature. The sum of inner cluster distances may be computed by setting various k values, and the optimal number of clusters may be determined by the Silhouette method and/or any other method of interpretation and validation of consistency within clusters. The medoids of all clusters may be selected as candidate features to construct prediction models (e.g., a cancer survival prediction model, etc.).

Regression 114 may be applied to clustered features (e.g., the features 132, etc.), for example, to determine a subsets of features that may be used for analysis (e.g., prognostic analysis, diagnostic analysis, etc.). Any type of regression analysis method/algorithm may be used to enhance the prediction accuracy and interpretability of the analytical model 120. For example, least absolute shrinkage and selection operator (LASSO) regression analysis may be used to select medoid features 115 from the clusters based respective associations with a determinative outcome, such as cancer survival. A LASSO algorithm may be expressed as:

$$\min_{\beta} \|y - X\beta\|_2^2 + \lambda \|\beta\|_1$$

where y denotes the survival outcome (1: alive, 0: dead), X is a vector containing all latent variables determined by the dimensional bottleneck (121), β denotes the coefficient of regression, and λ is the penalty coefficient. The L1-norm in the second term penalizes the selection of redundant variables. The parameter λ may be determined via cross validation on the training dataset. For example, latent variables that survived the L1-penalty with the best λ may be selected for the logistic regression model (114) to predict the survival outcome. LASSO-selected variables may be used with logistic regression to estimate the coefficients and predict a survival outcome.

Using the LASSO-selected variables, a logistic regression may be applied to estimate coefficients and predict survival outcome. The logistic regression can be expressed as follows:

$$y = \{1 + e^{-(\beta_0 + \Sigma_{i=1}^{n}(\beta_i x_i))}\}^{-1}$$

where y denotes the predicted survival probability; $x_i$ is the $i^{th}$ LASSO-selected feature, and $\beta_i$ is the regression coefficient.

The output from the convolutional encoder 121 may be decoded by the decoder 123 to produce a segmentation map 130. The segmentation map 130 may be a binary segmentation map where a 1 may represent a tumor, and a 0 may represent the non-existence of a tumor.

In some instances, performance of the system 100 (the prediction model 122), such as features determined and their respective prognostic (and/or diagnostic) value, may be measured via cross validation. For example, image data (the plurality of images, etc.) may be split into training and test sets. The analytical model 120 may be trained (as described) with the training set and the test sets may be left out for validation. For example, the analytical model 120 may be trained to predict subject/patient survival/death when a new image 111 depicting a tumoral state (e.g., metastasis, recurrence, development, etc.) affecting the subject/patient is provided to the trained convolutional encoder 121. The trained convolutional encoder 121 may produce encoded features that may be automatically classified, at 128, based on prognostic features learned during the training phase of the analytical model 120. The trained convolutional encoder 121 may encode features that may be automatically classified to output a prognosis, such as a survival prediction 129.

Figure 2A:
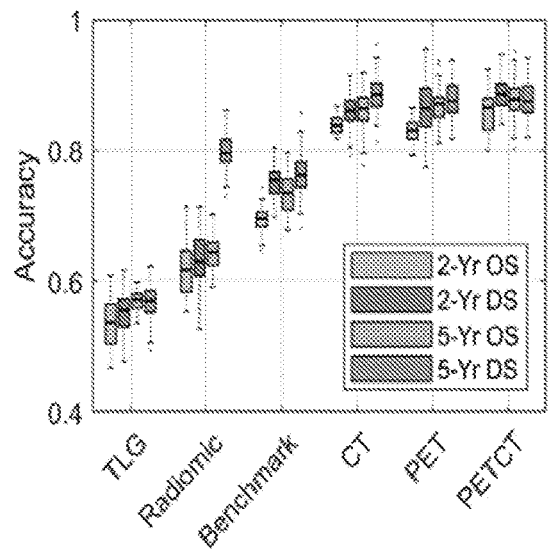
FIGS. 2A-2D show results generated by an example system for image segmentation and analysis.
Figure 2B:
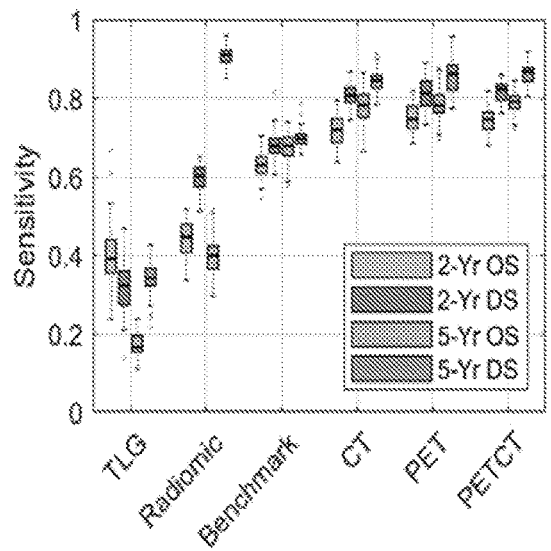
Figure 2C:
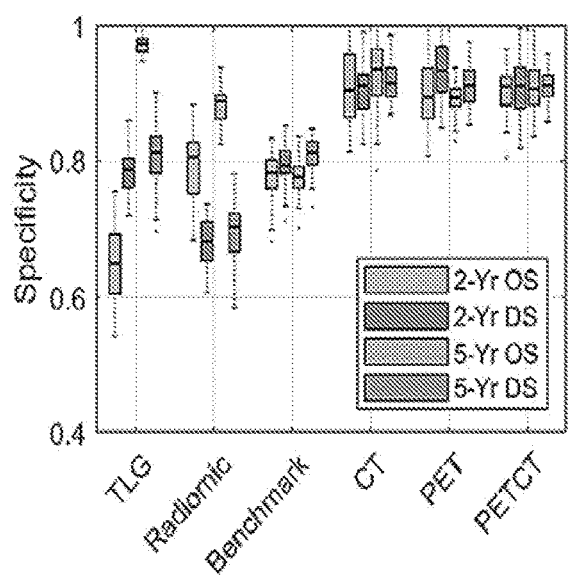
Figure 2D:
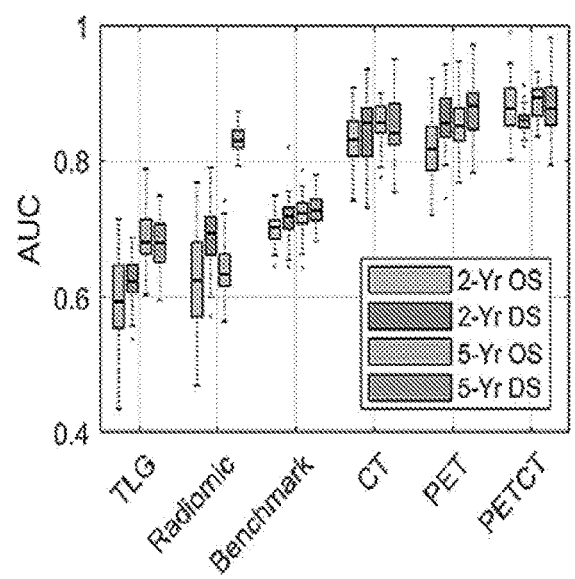

FIGS. 2A-2D illustrate the validated prognostic performance of the features extracted/determined by the convolutional encoder 121 where the analytical model 120 is trained to predict/determine cancer (tumor) survival/death. The performance of the analytical model 120 in predicting/determining cancer survival is based on four survival categories: 2-year overall survival (2-yr. OS), 5-year overall survival (5-yr. OS), 2-year disease-specific survival (2-yr. DS), and 5-year disease-specific survival (5-yr. DS). The features extracted/determined by the convolutional encoder 121, such as the maximum and the mean of standard uptake value (SUV) and total lesion glycolysis (TLG) for non-small-cell lung cancer (NSCLC), are compared to a conventional TLG metric, radiomics features (17) defined an existing machine learning model, and a benchmark convolutional neural network (CNN) prediction. Measures of accuracy, sensitivity, specificity, and the area under the curve (AUC) (e.g., the area under the receiver operating characteristic curve) for each survival category are determined. Box plots represent the average performance scores as indicted by the central mark and 25th and 75th percentiles across 6-fold cross validation experiments. FIG. 2A illustrates the overall prediction accuracy (proportion of the correct prediction over the entire dataset) of the system 100 analyzing PET/CT images in comparison to the TLG, radiomics, and benchmark features, FIG. 2B illustrates sensitivity (correct prediction of death over all death cases), FIG. 2C illustrates specificity (correct prediction of survival across all survival cases), and FIG. 2D illustrates AUC of the receiver operating characteristics (ROC) curve.

The estimated AUC of the predictive network 100 is 0.88 (95% CI: 0.80-0.96) for the prediction of 2 OS. For other survival criteria, the estimated AUCs are similar, namely 0.89 (95% CI: 0.85-0.93) for 5 OS, 0.86 (95% CI: 0.81-0.91) for 2 DS, and 0.88 (95% CI: 0.81-0.95) for 5 DS. The estimated AUC values of the conventional TLG and other radiomics markers range between 0.60 and 0.83 on the same dataset.

Figure 3A:
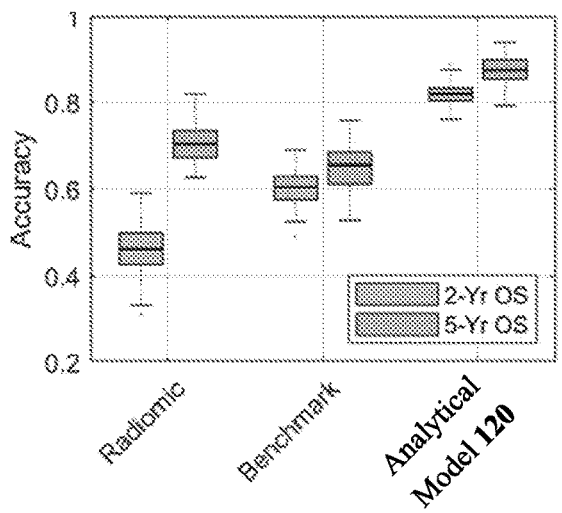
FIGS. 3A-3D show results generated by an example system for image segmentation and analysis.
Figure 3B:
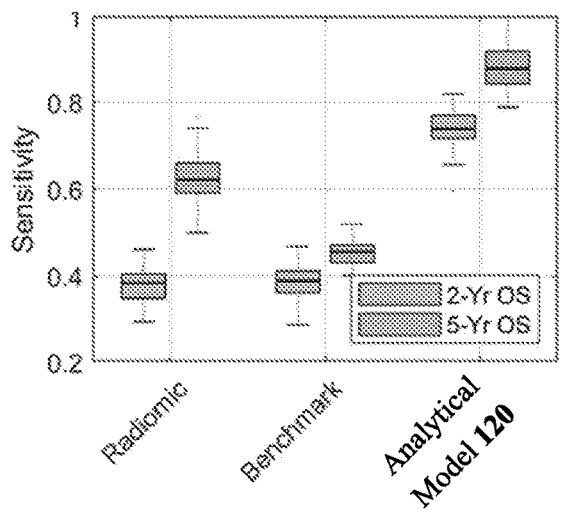
Figure 3C:
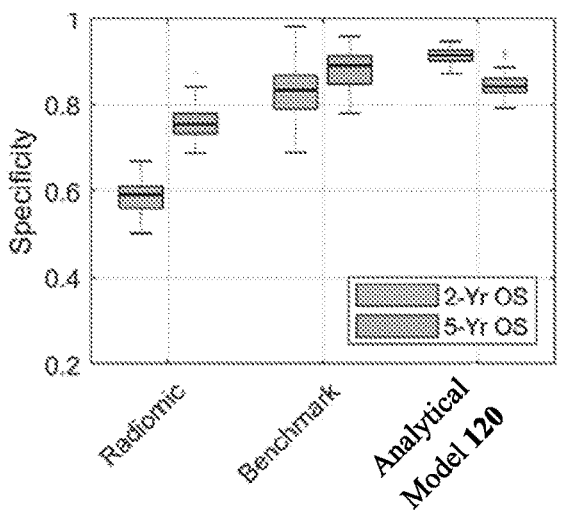
Figure 3D:
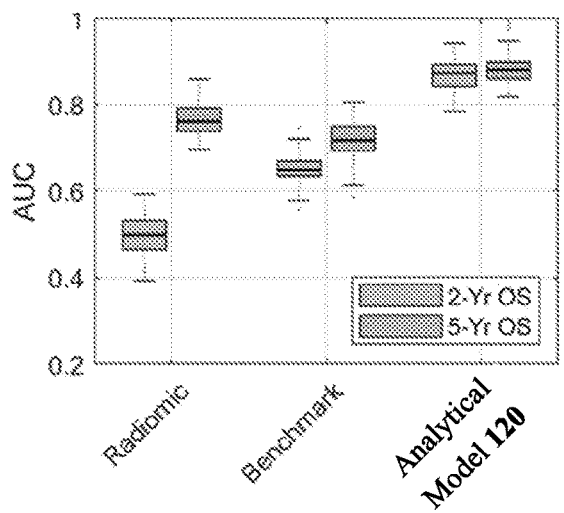

FIGS. 3A-3D illustrate the validated prognostic performance of the features extracted/determined by the convolutional encoder 121 where the analytical model 120 is trained to predict/determine cancer (tumor) survival/death and a different dataset is used for analysis and disease-specific survival information is not used. Performance of the analytical model 120 in predicting/determining cancer survival is based on two survival categories: 2-year overall survival (2-yr. OS) and 5-year overall survival (5-yr. OS). The features extracted/determined by the convolutional encoder 121 are compared to radiomics features (6) defined an existing machine learning model, and a benchmark convolutional neural network (CNN) prediction. Measures of accuracy, sensitivity, specificity, and the area under the receiver operating characteristic curve (AUC) per each survival category are determined. Box plots represent the average performance scores as indicted by the central mark and 25th and 75th percentiles based on the dataset. FIG. 3A illustrates the overall prediction accuracy (proportion of the correct prediction over the entire dataset) of the system 100 analyzing PET/CT images in comparison to the TLG, radiomics, and benchmark features, FIG. 3B illustrates sensitivity (correct prediction of death over all death cases), FIG. 3C illustrates specificity (correct prediction of survival across all survival cases), and FIG. 3D illustrates AUC of the receiver operating characteristics (ROC) curve. The estimated AUC of the predictive network 100 is 0.87 (95% CI: 0.80-0.94) for 2-yr. OS, and 0.90 (95% CI: 0.82-0.98) for 5-yr. OS.

Figure 4:
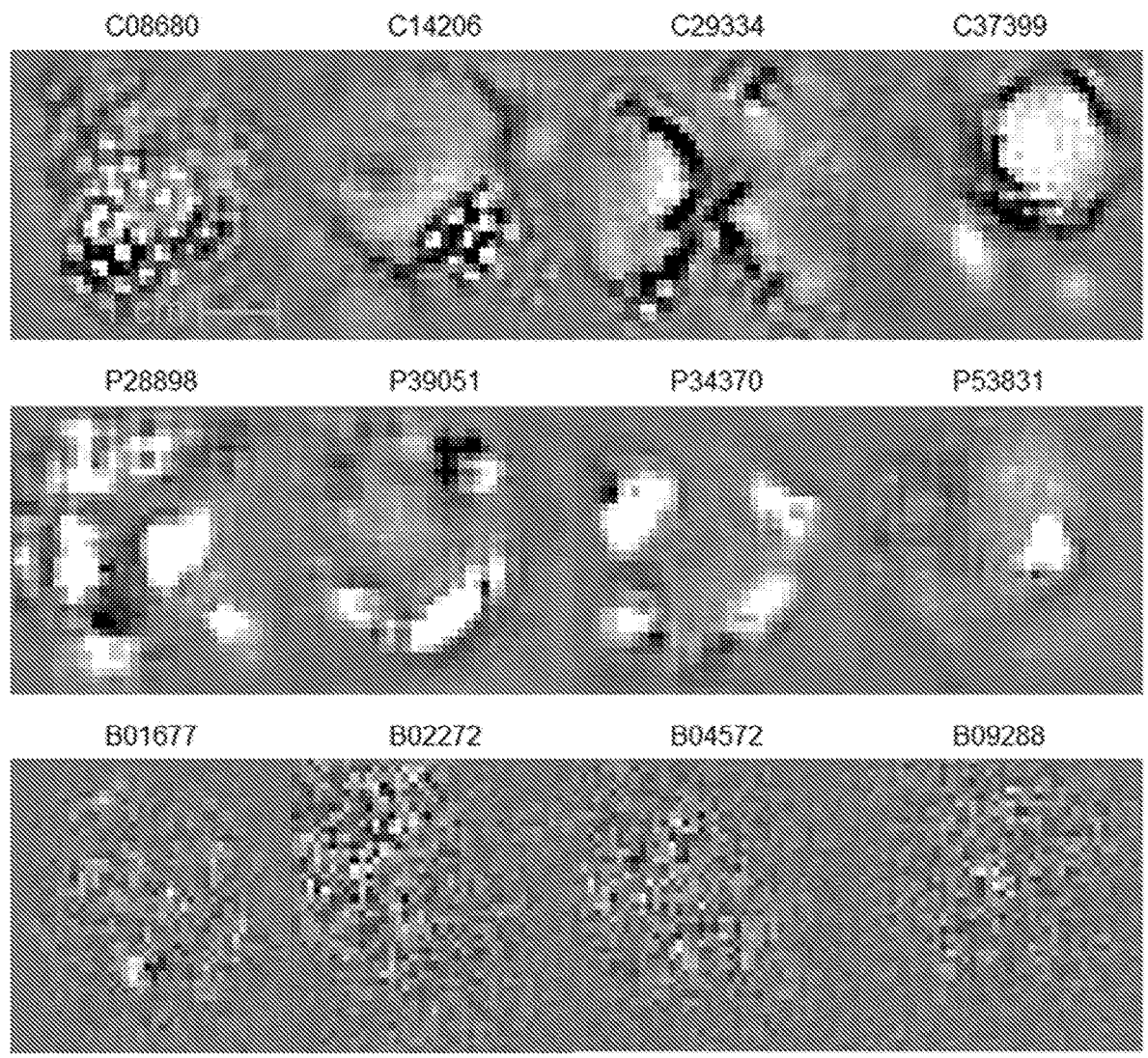
FIG. 4 shows imaged features generated by an example system for image segmentation and analysis.

The system 100 may enable features determined, learned, and/or extracted by the convolutional encoder 121 to be visualized. Features determined, learned, and/or extracted by the convolutional encoder 121 may be visualized to provide an intuitive understanding of what prognostic markers represent. An activation maximization scheme may be used to visualize LASSO-selected features from the convolutional encoder 121. For example, the features determined, learned, and/or extracted by the convolutional encoder 121 may be essentially artificial neurons in the deep neural network of the convolutional encoder 121. The neurons may be visualized by showing multitudes of image patterns and observing which image pattern activates a neuron most. For example, many different three-dimensional image patterns may be provided to the encoder network 121 and image patterns used to activate each neuron the most may be observed. An optimization-based approach may be employed, where the objective is to maximize individual neuron's activation by manipulating the input image pattern according to the following equation:

$$X^* = \underset{X}{\operatorname{argmax}}\, q(X \mid W, b)$$

where q(•|W, b) is the encoder network 121 with the trained model parameters W and b and X is the input image pattern. The equation may be solved for each individual neuron via gradient ascent:

$$X^{(k+1)} = X^{(k)} + \gamma^{(k)} \nabla q_i(X^{(k)})$$

where $X^{(k)}$ is the current solution at k-th iteration and $\gamma^{(k)}$ is a step length. $\gamma^{(k)}$ may be set as $1/\sigma^{(k)}$ where $\sigma^{(k)}$ denotes the standard deviation of the gradients. The gradient $\nabla q_i$ may be computed using a standard backpropagation algorithm. An initial image $X^{(0)}$ may be initialized with random voxel values following the Gaussian distribution $\mathcal{N}$ (128,1). FIGS. 4A-4B are the final solution (visualizations) X* after 20 iterations.

FIGS. 4A-4C shows visualizations of features determined, learned, and/or extracted by the convolutional encoder 121. The features determined, learned, and/or extracted by the convolutional encoder 121 are cancer survival-related features. In some instances, any features, related to any topic and/or area of analysis, may be determined, learned, and/or extracted by the convolutional encoder 121. During training, the analytical model 120 may learn "templates/patterns" from training images (e.g., the image 110, etc.) and apply the templates to analyze and understand new images (e.g., the image 111, etc.). C08680, C14206, C29334, and C37399 of FIG. 4A are image templates that the analytical model 120 (the convolutional encoder 121) determine for the segmentation task associated with computed tomography (CT) images. P28898, P39051, P34370, and P53831 of FIG. 4B are image templates that the analytical model 120 (the convolutional encoder 121) determine for the segmentation task associated with positron emission tomography (PET) images. The templates may be learned/determined in an unsupervised manner, without any survival-related information provided. The determined/learned templates are each survival-related and are characterized by their sensical and interpretable geometric structures. For example, C37399 is a template looking for and/or identifying a tumor-like shape at the top-right corner and a tube-like structure at the bottom-left. C08680 is a template looking for and/or identifying a textural feature of the tumor. B01677, B02272, B04572, and B09288 of FIG. 4C are image templates determined/learned by direct fitting of a machine learning model (e.g., a convolutional neural network, etc.) to survival data. As such, B01677, B02272, B04572, and B09288 are less interpretable than image templates that the analytical model 120 (the convolutional encoder 121) learn/determine.

The system 100 enables detailed visualizations of features with prognostic and/or diagnostic value. Regions of images (e.g., patient images, etc.) that may be used to determine a prognosis, such as a prediction of patient survival probability may be visualized based on guided gradient backpropagation. For example, one or more risk maps may be determined/generated and/or displayed by evaluating contribution to a prediction/prognosis of patient survival for each voxel of an input image/image data (e.g., the image 110, the image 111, etc.). For each voxel in the input image, with marginal change of the survival probability with respect to the voxel's intensity, defined as:

$$\frac{\partial P}{\partial x_{i,j,k}}.$$

A guided backpropagation algorithm may to compute $$\frac{\partial P}{\partial x_{i,j,k}}$$

where P is the probability of death and $x_{i,j,k}$ is a voxel value at the position (i,j,k) in an image (e.g., a patient image, the image 110, the image 111, etc.). The gradient $$\frac{\partial P}{\partial x_{i,j,k}}$$

can be interpreted as the change of the death probability when the voxel $x_{i,j,k}$ changes to a different value. If a voxel is not significant in predicting death, the corresponding gradient value would be small. In contrast, if the voxel played an important role in the death prediction, the corresponding gradient value would be greater.

In a guided backpropagation process, the gradient may be rectified by dropping the negative gradient values to focus on the "risk" by applying a rectified linear unit (ReLU) activation when the values are backpropagated from node to node of the bottleneck network 121,123 based on the flowing equation:

$$\alpha^{(m)} = \max\left(\frac{\partial(P)}{\partial A_{i,j,k}^{(m)}}, 0\right)$$

where $A^{(m)}$ denotes the activation map corresponding to the m-th convolutional kernel at the bottleneck network 121, 123. In some instances, only LASSO-selected features are included in the survival model P such that $$\frac{\partial P}{\partial x_{i,j,k}}$$

is routinely equal to zero (0). A risk map $\mathcal{R}$ may be defined as a linear combination of all activation maps at the bottleneck layer with the of coefficients $\alpha^{(m)}$ (as previous defined) based on the following:

$$\mathcal{R}(X) = \Sigma_m \alpha^{(m)} A^{(m)}(X).$$

Figure 5:
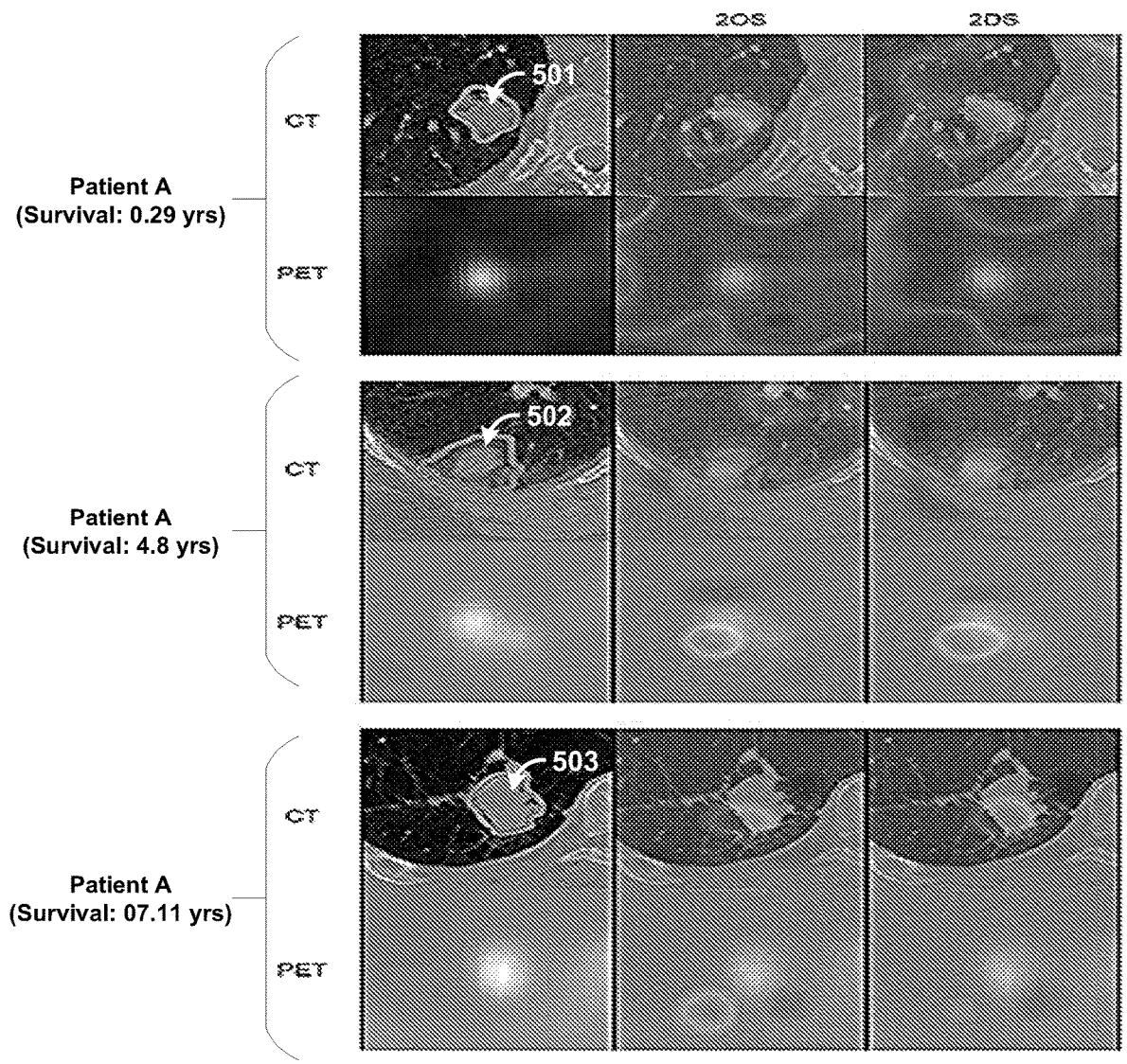
FIG. 5 shows imaged features generated by an example system for image segmentation and analysis.

The gradient may be displayed, for example, with heat maps (e.g., risk maps). FIG. 5 illustrates heat maps (e.g., risk maps) representing the gradient. Heated regions 501, 502, and 503 are areas (e.g., tumoral regions) that lowered the probability of patient survival whereas the other areas had negligible effect on patient survival. Notably some of the heated regions outside of the tumoral volume may match actual locations of recurrences and metastases when compared with post-therapeutic images and clinical records.

In some instances, visualized features may be used to identify regions of tumoral progression and/or recurrence. For example, visualized features (e.g., heat maps, etc.) may be compared to images and clinical records of the patients that receive stereotactic-body radiotherapy (SBRT). FIGS. 6A-6C, together, illustrate correlations between visualization enabled by the system 100 and cancer progression. Post-SBRT CT images are compared with the visualization results from the analytical model 120 (the convolutional encoder 121). FIGS. 6A-6C illustrate an agreement of the visualized heated regions with the actual location of tumoral recurrence. FIG. 6A illustrates a three-dimensional (3D) rendering showing the location of a primary tumor volume 602 and the tumoral progression region 604 within a patient. FIG. 6B illustrates pre-SBRT transversal slices at the primary tumor location (images 606A-606C), 3 centimeters below (images 608A-608C), and 5 centimeters below (images 610A-610C) based on a CT image, a PET image, and Heat map visualization determined by the system 100. FIG. 6C illustrates a post-SBRT image of the same patient. The dashed box 612 indicates the estimated corresponding ROI to the primary (pre-SBRT) CT slices. The heat map generated based on pre-SBRT, i.e., the same heat map as in the bottom row of (b), is superimposed on top of the ROI on the post-SBRT image. Notice that the recurrence location coincides with the heated area.

The segmentation algorithm employed by the analytical model 120, when trained by PET/CT images (or any other imaging modality) for automated tumor segmentation, codifies rich structural and functional geometry at the bottleneck layer 121,123. Codified features may be used for survival prediction in cancer patients without a need to train the analytical model 120 with survival-related information. Visualizations determined by the system 100 are a practical, clinical tool for patient-tailored treatment planning. Features determined by the analytical model 120 (the convolutional encoder 121) capture sensical and interpretable geometric shapes from the images, such as tumor-like blobs or heterogeneity of a tumor (e.g. C08680, etc.). Features determined by the analytical model 120 (the convolutional encoder 121) may identify tube-like structures nearby tumor-like blobs, which may capture blood vessels and lymphatics in the peritumoral area. As shown, the analytical model 120 provides generalizable features and rules for making prognostic prediction. In some instances, the analytical model 120 may be trained to perform any other image segmentation and/or analysis task. The system 100 (the analytical model 120) may generate, based on image data, any features that may be visualized and provide extensive prognostic value.

In an embodiment, illustrated in FIG. 7, the system 100, and/or any other device/component described herein can be configured to perform a method 700. At 710, a plurality of medical images may be received from a database. The plurality of medical images may include two-dimensional (2D) images, three-dimensional (3D) images, and/or any type of image. For example, plurality of medical images may include computed tomography (CT) images, positron emission tomography (PET) images, magnetic resonance imaging (MRI) images, ultrasound images, elastography images, combinations thereof, and or the like. In some instances, the plurality of images may be associated with non-small-cell lung cancer (NSCLC) patients.

At 720, a binary mask associated with an object of interest in each medical image may be generated for each of the plurality of medical images. Generating each binary mask may include modifying each of the plurality of medical images to indicate a region of interest in each medical image based on an object of interest in each medical image. For example, the object of interest in each medical image may be a tumor. Each binary mask associated with the object of interest in each medical image may be indicative of one or more voxels associated with the object of interest.

At 730, the plurality of medical images and the generated binary mask for each medical image may be provided to an untrained predictive model (e.g., the analytical model 120, etc.). The plurality of medical images and the generated binary mask for each medical image may be used to train the predictive model (e.g., to generate/produce a trained predictive model).

At 740, the untrained predictive model may determine, for each of the plurality of medical images, one or more latent parameters (e.g., the features 132, etc.) associated with the object of interest in each medical image. Determining the one or more latent parameters associated with the object of interest in each medical image may include two steps. First, the untrained predictive model may be used to determine, for each of the plurality of medical images, a plurality of parameters associated with the object of interest in each medical image. Second, a clustering algorithm (e.g., k-medoids clustering, etc.) and a regression method (e.g, LASSO regression, etc.) may be applied to the plurality of parameters associated with the object of interest in each medical image to determine the one or more latent parameters associated with the object of interest in each medical image.

At 750, a trained predictive model may be generated. The trained predictive model may be generated based on the one or more latent parameters associated with the object of interest in each of the plurality of medical images. For example, the one or more latent parameters associated with the object of interest in each of the plurality of medical images may be used to form one or more datasets. The one or more datasets may be provided to the untrained predictive model to teach the predictive model to identify latent parameters associated with and/or similar to the one or more latent parameters associated with the object of interest in each of the plurality of medical images. In some instances, the trained predictive model may be used to generate a prognosis, such as a survival probability for a patient.

At 760, one or more images associated with latent parameters (e.g., features, etc.) may be displayed. The one or more images may be indicative of a prognosis. For example, the one or more images may indicate a survival probability for the patient, such as a patient affected by NSCLC. To determine the survival probability for the patient, the predictive model may receive a medical image associated with the patient. The medical image may indicate an object of interest, such as a tumor and/or the like. The predictive model may generate latent parameters (associated with the object of interest) at one or more layers of a convolutional neural network included with the predictive model. To reduce the amount of latent parameters analyzed at a layer of the predictive model, a clustering algorithm and/or regression method may be applied to the latent parameters determined at the layer to determine a subset of latent parameters. The one or more images associated with latent parameters may include one or more heat maps (e.g., risk maps, etc.). The one or more heat maps associated with the subset of latent parameters may be generated and displayed so that subset of latent parameters may be visualized. The one or more heat maps may indicate a prognosis, such as the survival probability for the patient.

In an embodiment, illustrated in FIG. 8, the system 100, and/or any other device/component described herein can be configured to perform a method 800 comprising, at 810, a medical image (e.g., a two-dimensional (2D) image, a three-dimensional (3D) image, etc.) may be received. A predictive model (e.g., the analytical model 120, etc.) comprising a plurality of layers may receive the medical image. In some instances, the medical image may be modified to indicate a region of interest (ROI) based on the object of interest. The medical image may include any type of image. For example, the medical image may include a computed tomography (CT) image, a positron emission tomography (PET) image, a magnetic resonance imaging (MRI) image, an ultrasound image, an elastography image, combinations thereof, and or the like. In some instances, the predictive model may include a convolutional neural network (CNN) and the one or more layers of the plurality of layers may include convolutional layers of the CNN. The medical image may include an object of interest, such as an identified tumor/tumor tissue. The medical image may include any object of interest. The medical image may be modified to include a region-of-interest (ROI). The ROI may be an area associated with and/or in proximity to the object of interest.

At 820, a plurality of features associated with an object of interest in the medical image may be determined. The predictive model may determine, at each of one or more layers of the plurality of layers, a plurality of features associated with an object of interest in the medical image. The predictive model may include an encoder-decoder network (e.g., a bottleneck network, etc.) where the encoder network, at each layer, maps raw inputs to feature representations. The encoder network may include a plurality of layers (convolutional layers) that each include a plurality of neurons. Each neuron may determine features of the plurality of features. The plurality of features may be associated with the object of interest and/or the ROI. For example, the features of the plurality of features may include one or more geometric shapes from the medical image, such as tumor-like blobs. In some instances, the features of the plurality of features may indicate heterogeneity of a tumor within a subject/patient.

At 830, a subset of features of the plurality of features may be determined. The predictive model may determine a subset of features of the plurality of features determined for a layer of the one or more layers. The layer may include a plurality of neurons. In some instances, determining the subset of features may include unsupervised k-medoids clustering of the plurality of features to reduce the amount/quantity of features of the plurality of features. Any other clustering algorithm may be used to reduce the amount/quantity of the plurality of features. Least absolute shrinkage and selection operator (LASSO) regression may be applied to the reduced amount/quantity of features to determine the subset of features. In some instances, any regression method/algorithm may be applied to the reduced amount/quantity of features to determine the subset of features. Any feature selection method/algorithm may be used to determine the subset of features, such as any wrapper feature selection method, any filter feature selection method, any embedded feature selection method, and/or the like. In some instances, a decoder network may receive feature representations (the subset of features, etc.) produced by an encoder network as input and process the feature representations to output a prognosis/prediction, such as patient survival/death and/or the like.

At 840, one or more images associated with the subset of features may be displayed. Each image of the one or more images may be associated with a neuron of the one or more neurons. In some instances, an activation maximization function may be applied to the subset of features to determine the one or more neurons of the plurality of neurons. A backpropagation algorithm may be applied to gradients produced by the activation maximization function to generate one or more heat maps. The one or more heat mays may be displayed. The one or more heat maps may indicate a prognosis, such as a survival/death probability for a subject/patient.

Figure 9:
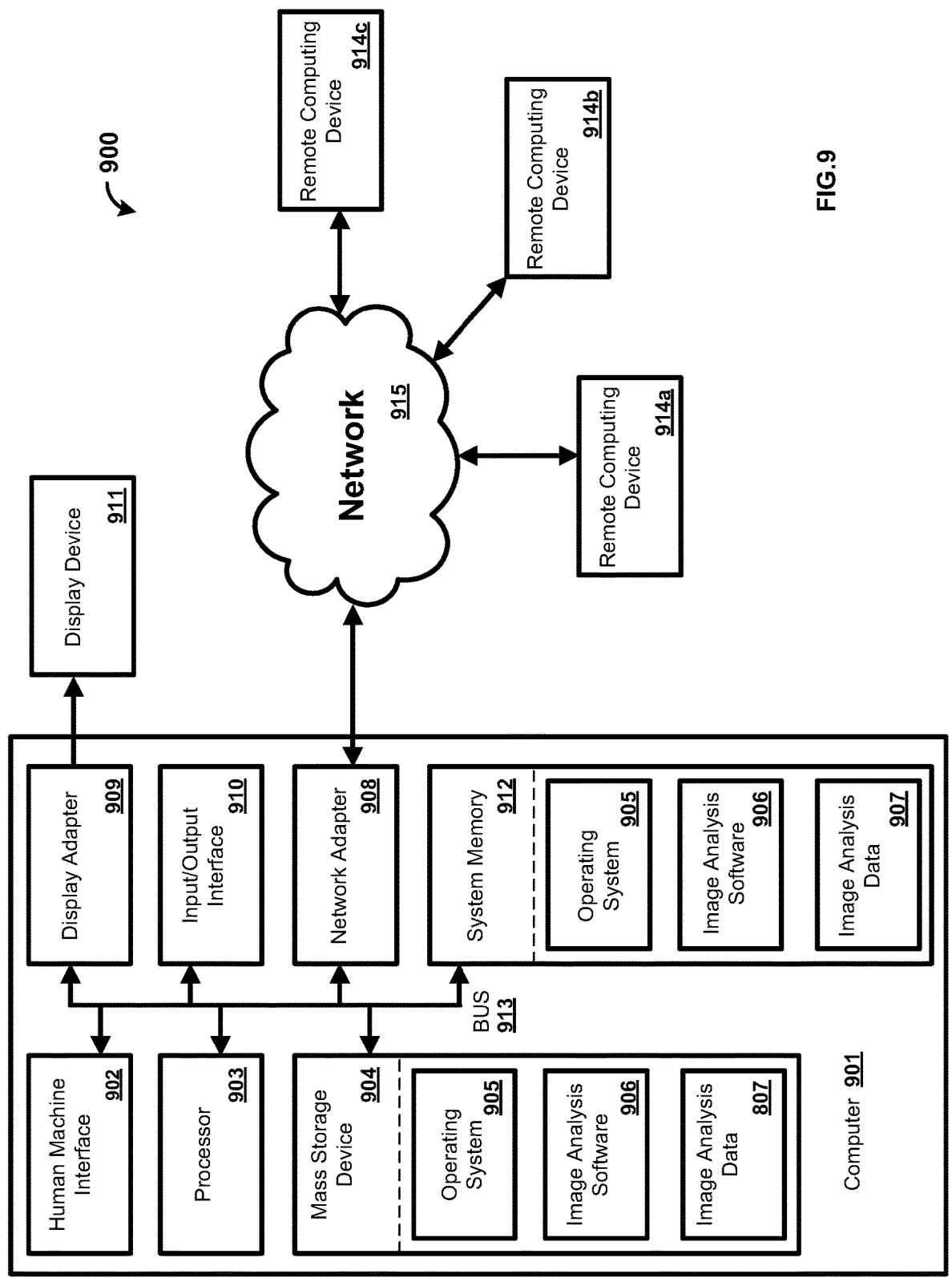
FIG. 9 shows a block diagram of a computing device for implementing image segmentation and analysis.

FIG. 9 shows a system 900 for image segmentation and analysis in accordance with the present description. The any device, portion, and/or component of the system 100 of FIG. 1 may be a computer 901 as shown in FIG. 9. The computer 901 may comprise one or more processors 903, a system memory 912, and a bus 913 that couples various system components including the one or more processors 903 to the system memory 912. In the case of multiple processors 903, the computer 901 may utilize parallel computing. The bus 913 is one or more of several possible types of bus structures, including a memory bus or memory controller, a peripheral bus, an accelerated graphics port, or local bus using any of a variety of bus architectures.

The computer 901 may operate on and/or comprise a variety of computer readable media (e.g., non-transitory media). The readable media may be any available media that is accessible by the computer 901 and may include both volatile and non-volatile media, removable and non-removable media. The system memory 912 has computer readable media in the form of volatile memory, such as random access memory (RAM), and/or non-volatile memory, such as read only memory (ROM). The system memory 912 may store data such as the image analysis data 907 and/or program modules such as the operating system 905 and the image analysis software 906 that are accessible to and/or are operated on by the one or more processors 903.

The computer 901 may also have other removable/non-removable, volatile/non-volatile computer storage media. FIG. 9 shows the mass storage device 904 which may provide non-volatile storage of computer code, computer readable instructions, data structures, program modules, and other data for the computer 901. The mass storage device 904 may be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules may be stored on the mass storage device 904, such as the operating system 905 and the image analysis software 906. Each of the operating system 905 and the image analysis software 906 (e.g., or some combination thereof) may have elements of the program modules and the image analysis software 906. The image analysis data 907 may also be stored on the mass storage device 904. The image analysis data 907 may be stored in any of one or more databases known in the art. Such databases may be DB2®, Microsoft® Access, Microsoft® SQL Server, Oracle®, mySQL, PostgreSQL, and the like. The databases may be centralized or distributed across locations within the network 915.

A user may enter commands and information into the computer 901 via an input device (not shown). Examples of such input devices comprise, but are not limited to, a keyboard, pointing device (e.g., a computer mouse, remote control), a microphone, a joystick, a scanner, tactile input devices such as gloves, and other body coverings, motion sensor, and the like These and other input devices may be connected to the one or more processors 903 via a human machine interface 902 that is coupled to the bus 913, but may be connected by other interface and bus structures, such as a parallel port, game port, an IEEE 1394 Port (also known as a Firewire port), a serial port, network adapter 908, and/or a universal serial bus (USB).

The display device 911 may also be connected to the bus 913 via an interface, such as the display adapter 909. It is contemplated that the computer 901 may have more than one display adapter 909 and the computer 901 may have more than one display device 911. The display device 911 may be a monitor, an LCD (Liquid Crystal Display), light emitting diode (LED) display, television, smart lens, smart glass, and/or a projector. In addition to the display device 911, other output peripheral devices may be components such as speakers (not shown) and a printer (not shown) which may be connected to the computer 901 via the Input/Output Interface 910. Any step and/or result of the methods may be output (or caused to be output) in any form to an output device. Such output may be any form of visual representation, including, but not limited to, textual, graphical, animation, audio, tactile, and the like. The display device 911 and computer 901 may be part of one device, or separate devices.

The computer 901 may operate in a networked environment using logical connections to one or more remote computing devices 914a,b,c. A remote computing device may be a personal computer, computing station (e.g., workstation), portable computer (e.g., laptop, mobile phone, tablet device), smart device (e.g., smartphone, smart watch, activity tracker, smart apparel, smart accessory), security and/or monitoring device, a server, a router, a network computer, a peer device, edge device, and so on. Logical connections between the computer 901 and a remote computing device 914a,b,c may be made via a network 915, such as a local area network (LAN) and/or a general wide area network (WAN). Such network connections may be through the network adapter 908. The network adapter 908 may be implemented in both wired and wireless environments. Such networking environments are conventional and commonplace in dwellings, offices, enterprise-wide computer networks, intranets, and the Internet.

Application programs and other executable program components such as the operating system 905 are shown herein as discrete blocks, although it is recognized that such programs and components reside at various times in different storage components of the computing device 901, and are executed by the one or more processors 903 of the computer. An implementation of the image analysis software 906 may be stored on or sent across some form of computer readable media. Any of the described methods may be performed by processor-executable instructions embodied on computer readable media.

Embodiment 1: A method comprising: receiving, by a predictive model comprising a plurality of layers, a medical image, determining, at each of one or more layers of the plurality of layers, a plurality of features associated with an object of interest in the medical image, determining a subset of features of the plurality of features determined for a layer of the one or more layers, wherein the layer comprises a plurality of neurons, and causing, based on one or more neurons of the plurality of neurons, display of one or more images associated with the subset of features, wherein each image of the one or more images is associated with a neuron of the one or more neurons.

Embodiment 2: The embodiment as in any one of the preceding embodiments wherein the predictive model comprises a convolutional neural network, wherein the one or more layers of the plurality of layers comprise convolutional layers of the convolutional neural network.

Embodiment 3: The embodiment as in any one of the preceding embodiments, wherein the predictive model comprises an encoder-decoder network.

Embodiment 4: The embodiment as in any one of the preceding embodiments, wherein determining the subset of features is based on one or more of k-medoids clustering, least absolute shrinkage and selection operator (LASSO) regression, a wrapper feature selection algorithm, or a filter feature algorithm.

Embodiment 5: The embodiment as in any one of the preceding embodiments further comprising determining, based on the one or more images associated with the subset of features, a prognosis.

Embodiment 6: The embodiment as in the embodiment 5, wherein the prognosis is associated with one or more of survival of a subject, death of the subject, or health of the subject.

Embodiment 7: The embodiment as in any one of the preceding embodiments further comprising modifying the medical image to indicate a region of interest (ROI) based on the object of interest.

Embodiment 8: The embodiment as in the embodiment 7, wherein the plurality of features associated with the object of interest determined at each of the one or more layers are associated with the ROI.

Embodiment 9: The embodiment as in any one of the preceding embodiments, wherein the plurality of features associated with the object of interest determined at each of the one or more layers indicate one or more of a functional geometry associated with the object of interest or a structural geometry associated with the object of interest.

Embodiment 10: The embodiment as in any one of the preceding embodiments, wherein the layer of the one or more layers comprises a bottleneck layer.

Embodiment 11: The embodiment as in any one of the preceding embodiments further comprising determining, based on an activation maximization function, the one or more neurons.

Embodiment 12: The embodiment as in any one of the preceding embodiments, wherein the one or more images associated with the subset of features comprise one or more heat maps associated with the object of interest.

Embodiment 13: The embodiment as in any one of the preceding embodiments, wherein the medical image comprises one or more of a computed tomography (CT) image, a positron emission tomography (PET) image, a magnetic resonance imaging (MRI) image, an ultrasound image, or a elastography image.

Embodiment 14: The embodiment as in any one of the preceding embodiments further comprising: determining, based on a plurality of medical images and a binary mask associated with an object of interest in each medical image of the plurality of medical images, a dataset, and training, based on the plurality of medical images and the dataset, the predictive model.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
receiving, by a predictive model comprising a plurality of layers, a medical image;
determining, at each of one or more layers of the plurality of layers, a plurality of features associated with an object of interest in the medical image, wherein the medical image comprises a plurality of voxels defining a first pattern associated with the object of interest;
generating, based on at least one modification to at least one voxel of the plurality of voxels, a plurality of generated image patterns that each differ at least partially from the first pattern;
determining, based on the plurality of generated image patterns, a subset of features of the plurality of features associated with a first layer of the one or more layers, wherein the first layer comprises a plurality of neurons, and wherein the at least one modification to the at least one voxel is associated with a maximized activation of one or more neurons of the plurality of neurons; and
causing, based on the maximized activation of the one or more neurons, display of one or more generated image patterns, of the plurality of generated image patterns, associated with the subset of features and the maximized activation of the one or more neurons.

2. The method of claim 1, wherein the predictive model comprises a convolutional neural network, wherein the one or more layers of the plurality of layers comprise convolutional layers of the convolutional neural network.

3. The method of claim 1, wherein determining the subset of features is based on one or more of k-medoids clustering, least absolute shrinkage and selection operator (LASSO) regression, a wrapper feature selection algorithm, or a filter feature algorithm.

4. The method of claim 1 further comprising modifying the medical image to indicate a region of interest (ROI) based on the object of interest, wherein the plurality of features associated with the object of interest determined at each of the one or more layers are associated with the ROI.

5. The method of claim 1, wherein the plurality of features associated with the object of interest determined at each of the one or more layers indicate one or more of a functional geometry associated with the object of interest or a structural geometry associated with the object of interest.

6. The method of claim 1, wherein the one or more generated image patterns associated with the subset of features comprise one or more heat maps associated with the object of interest.

7. The method of claim 1 further comprising:
determining, based on a plurality of medical images and a binary mask associated with an object of interest in each medical image of the plurality of medical images, a dataset; and
training, based on the plurality of medical images and the dataset, the predictive model.

8. An apparatus comprising:
one or more processors; and
memory storing processor executable instructions that, when executed by the one or more processors, cause the apparatus to:
receive a medical image;
determine, at each of one or more layers of a plurality of layers, a plurality of features associated with an object of interest in the medical image, wherein the medical image comprises a plurality of voxels defining a first pattern associated with the object of interest;
generate, based on at least one modification to at least one voxel of the plurality of voxels, a plurality of generated image patterns that each differ at least partially from the first pattern;
determine, based on the plurality of generated image patterns, a subset of features of the plurality of features associated with a first layer of the one or more layers, wherein the first layer comprises a plurality of neurons, and wherein the at least one modification to the at least one voxel is associated with a maximized activation of one or more neurons of the plurality of neurons; and
cause, based on the maximized activation of the one or more neurons, display of one or more generated image patterns, of the plurality of generated image patterns, associated with the subset of features and the maximized activation of the one or more neurons.

9. The apparatus of claim 8, wherein the one or more layers of the plurality of layers comprise convolutional layers of a convolutional neural network.

10. The apparatus of claim 8, wherein the processor executable instructions that, when executed by the one or more processors, cause the apparatus to determine the subset of features further cause the apparatus to determine the subset of features based on one or more of k-medoids clustering, least absolute shrinkage and selection operator (LASSO) regression, a wrapper feature selection algorithm, or a filter feature algorithm.

11. The apparatus of claim 8, wherein the processor executable instructions, when executed by the one or more processors, further cause the apparatus to modify, based on the object of interest, the medical image to indicate a region of interest (ROI), wherein the plurality of features associated with the object of interest determined at each of the one or more layers are associated with the ROI.

12. The apparatus of claim 8, wherein the plurality of features associated with the object of interest determined at each of the one or more layers indicate one or more of a functional geometry associated with the object of interest or a structural geometry associated with the object of interest.

13. The apparatus of claim 8, wherein the one or more generated image patterns associated with the subset of features comprise one or more heat maps associated with the object of interest.

14. The apparatus of claim 8, wherein the processor executable instructions, when executed by the one or more processors, further cause the apparatus to:

determine, based on a plurality of medical images and a binary mask associated with an object of interest in each medical image of the plurality of medical images, a dataset; and train, based on the plurality of medical images and the dataset, a predictive model.

15. A non-transitory computer readable medium comprising processor-executable instructions that, when executed by one or more processors, cause the one or more processors to:

receive a medical image;

determine, at each of one or more layers of a plurality of layers, a plurality of features associated with an object of interest in the medical image, wherein the medical image comprises a plurality of voxels defining a first pattern associated with the object of interest;

generate, based on at least one modification to at least one voxel of the plurality of voxels, a plurality of generated image patterns that each differ at least partially from the first pattern;

determine, based on the plurality of generated image patterns, a subset of features of the plurality of features associated with a first layer of the one or more layers, wherein the first layer comprises a plurality of neurons, and wherein the at least one modification to the at least one voxel is associated with a maximized activation of one or more neurons of the plurality of neurons; and cause, based on the maximized activation of the one or more neurons, display of one or more generated image patterns, of the plurality of generated image patterns, associated with the subset of features and the maximized activation of the one or more neurons.

16. The non-transitory computer readable medium of claim 15, wherein the one or more layers of the plurality of layers comprise convolutional layers of a convolutional neural network.

17. The non-transitory computer readable medium of claim 15, wherein the processor-executable instructions that cause the one or more processors to determine the subset of features further cause the one or more processors to determine the subset of features based on one or more of k-medoids clustering, least absolute shrinkage and selection operator (LASSO) regression, a wrapper feature selection algorithm, or a filter feature algorithm.

18. The non-transitory computer readable medium of claim 15, wherein the processor-executable instructions further cause the one or more processors to modify, based on the object of interest, the medical image to indicate a region of interest (ROI), wherein the plurality of features associated with the object of interest determined at each of the one or more layers are associated with the ROI.

19. The non-transitory computer readable medium of claim 15, wherein the plurality of features associated with the object of interest determined at each of the one or more layers indicate one or more of a functional geometry associated with the object of interest or a structural geometry associated with the object of interest.

20. The non-transitory computer readable medium of claim 15, wherein the one or more generated image patterns associated with the subset of features comprise one or more heat maps associated with the object of interest.

* * * * *